United States Patent [19]

Sondahl et al.

[11] Patent Number: 5,196,636
[45] Date of Patent: Mar. 23, 1993

[54] HIGH YIELD SWEET CORN HYBRID

[75] Inventors: Maro R. Sondahl, Cherry Hill, N.J.; William J. Da Silva, Campinas; Tharcizio C. De Almeida, Riberao Preto, both of Brazil

[73] Assignee: DNA Plant Technology Corporation, Cinnaminson, N.J.

[21] Appl. No.: 222,474

[22] Filed: Jul. 21, 1988

[51] Int. Cl.$^5$ ............................ A01H 5/00; A01H 1/00
[52] U.S. Cl. ................................. 800/205; 800/200; 800/235; 800/DIG. 55; 800/DIG. 56; 47/58
[58] Field of Search ................ 800/1, 205, 200; 47/58, 47/DIG. 1, 58

[56] References Cited

PUBLICATIONS

Ricci et al (1985) Reuista Industrial y Agricolade Tucuman, Jon-Jun vol. 62(1) pp. 13-22.
U.S. Pat. 3,971,161 to Bonucci
U.S. Pat. 4,630,393 to Bonucci.
Brown et al., in Corn and Corn Improvement: 51-88 (G. F. Sprague ed. 1977).
Salunkhe et al. eds, Postharvest Biotechnology of Cereals: 93 (1985).
Zuber et al., Corn: Chemistry and Technology: 31-51 (Watson et al. eds. 1987).
Kaukis et al., in Breeding Vegetable Crops: 475-519 (M. J. Bassett ed. 1986).
Boyer et al., in Plant Breeding Reviews: 139-159 (J. Janick ed.).
Creech, R. G., Genetics 52: 1175-1186 (1965).
Holder et al., Crop Science 14: 643-646 (1974).
Holder et al., Crop Science 14: 647-648 (1974).
Garwood et al., J. Amer. Soc. Hort. Sci. 101 (4): 400-404 (1976).
Wolf et al., Proc. Fla. State Hort. Soc. 90: 410-411 (1977).
Alexander, in Corn and Corn Improvement, 3d Ed., G. F. Sprague and J. W. Dudley, eds., American Society of Agronomy, Madison, Wisc., 1988, p. 869.

Primary Examiner—Howard J. Locker
Assistant Examiner—Gary Benzion
Attorney, Agent, or Firm—Pennie & Edmonds

[57] ABSTRACT

The present invention relates to novel sweet or supersweet corn hybrids with improved yield and germination characteristics. The hybrids of the present invention are produced by crossing flint and dent field corn parents.

21 Claims, 1 Drawing Sheet

HIGH YIELD SWEET CORN HYBRID

TABLE OF CONTENTS

1 Field of the Invention
2. Background of the Invention
  2.1. Sweet Corn
  2.2. Supersweet Corn
3. Brief Description of the Invention
4. Brief Description of the Figures
5. Detailed Description of the Invention
  5.1. Characteristics of High Yield Hybrids
  5.2. Dent Corn
  5.3. Flint Corn
  5.4. Flint x Dent Hybrids
  5.4.1 Supersweet SuSush2sh2
6. Example 1: Intervarietal Hybrid
  6.1. Supersweet Orange Flint Synthetic
    6.1.1. Population Synthesis
    6.1.2. Introduction of the sh2 Gene
    6.1.3. Recurrent Selection
  6.2. Supersweet Orange Dent Synthetic
    6.2.1. Population Synthesis
    6.2.2. Introduction of the sh2 Gene
    6.2.3. Recurrent Selection
7. Example 2: Top Cross Hybrid
  7.1. Improved Supersweet Orange Flint Synthetic
  7.2. Inbred Line MT-107 sh2
8. Example 3: Dried Corn Product

FIELD OF THE INVENTION

The present invention relates to new corn hybrids having improved characteristics of sweetness and yield. Specifically, the invention relates to hybrids having sugar content equivalent to or greater than typical sweet corn varieties, while having the desirable agronomic characteristics of a normal field corn variety.

BACKGROUND OF THE INVENTION

2.1. SWEET CORN

Maize (Zea mays) or corn has long been one of the most important food crops in the Western hemisphere being grown for both human and animal consumption. Because of the importance of the crop, corn breeders have focused a great deal of attention on improvement of a number of generally valuable characteristics, such as yield, tolerance of environmental stress, and disease and insect resistance. In specific connection with human consumption, particular efforts have been devoted to the development of a product with an improved taste, especially with respect to increasing the sweetness of the kernels. The most active area of research has been centered around manipulation of the endosperm genes which, to a large extent, control the level of sugar found in the kernel. Of particular interest is the "sugary" allele (su), a recessive mutation of the Su locus on chromosome 4. Sweet corn, by present definition, is homozygous for the recessive allele at this locus. This mutation is associated with the production of large amounts of water soluble polysaccharide (WSP), increased sugars, and greatly reduced amounts of starch, in comparison with field corn varieties. Both the WSP and sugar content significantly contribute to the consumer's perception of the desirable "sweet corn" taste, and both are also important in providing a product which is suitable for industrial processing, e.g., canning and freezing.

2.2. SUPERSWEET CORN

Although the su allele does provide a number of useful traits, sweet corn is not without its problems, and the presence of the allele in the homozygous condition does not alone necessarily produce a product which is completely satisfactory. For example, although the presence of the su allele will increase the sugar content of the endosperm to some extent, the percentage increase is not so substantial as to yield what would be considered a truly high sugar or "supersweet" product; for example, the difference between normal and sweet may be small, e.g., as little as 4.8% being average for normal, and 13.1% for sweet corn, at 24 days after pollination (Creech, R. G., *Genetics* 52: 1175–1186, 1965). Moreover, sweet corn tends to be less hardy than field corn, having lower overall yields and germination rates, and producing seed which may be more susceptible to mechanical damage and seed borne microorganisms than field corn (Kaukis et. al., *in Breeding Vegetable Crops*, AVI Publishing Co., 1986, p. 475–519). Susceptibility to insect damage and microorganisms also results in a lower percentage of usable ears, which ultimately is as important a characteristic as overall yield. For this reason, there has been a substantial amount of effort invested in finding ways of augmenting the higher levels of sugar by developing new genetic combinations of other endosperm genes with the sugary allele. The mutation sh2 at the shrunken-2 genetic locus has been shown to have a desirable interaction with the su allele with respect to increasing the amount of sugar in the endosperm (Holder, et. al., *Crop Science*, 14: 643, 1974), but with a concomitant reduction in the amount of WSP, endosperm and starch. Typical amounts of WSP in normal sweet corn is about 28.5% (Creech, R. G., *Genetics* 52: 1175–1186, 1965). Thus, the genotype susush$_2$sh$_2$, although having increased sweetness, also produces seed which is lightweight, easily damaged and therefore difficult to germinate. Attempts to improve the vigor of the genotype by using dent (field) corn as the background for the sh$_2$ allele results in the necessity for isolation of the hybrid from both sweet and field corn. U.S. Pat. No. 3,971,161 describes a hybrid sweet corn having the genotype susuSh$_2$Sh$_2$, derived from a cross between parents both having a sweet corn background. The hybrid is said to be high in sugar and to increase WSP; however, it is not as high in sugar as sh$_2$ hybrids. Similarly, U.S. Pat. No. 4,630,393 describes a sweet corn hybrid having the genotype Susush$_2$sh$_2$, which is produced by a cross between a shrunken sweet corn parent (susush$_2$sh$_2$) and a dent shrunken parent (SuSush$_2$sh$_2$). However, the use of even one parent with a sweet corn background still gives rise to the usual problems associated with sweet corn, i.e., reduced germination and yield, susceptibility to foliar diseases such as blights, rusts and virus, and low insect resistance, among others. It would thus appear from the efforts described in the literature that in order to obtain a sweet corn product with the desired sugar content and superior agronomic traits, it is necessary to sacrifice many of the desirable field corn characteristics in favor of having at least one sweet corn parent.

It has now been unexpectedly discovered that it is possible to obtain a hybrid having sugar levels equivalent to or greater than those described for known sweet and supersweet corn lines, while at the same time retaining the favorable field corn attributes of hardiness and good yield. These novel hybrids are obtained by using parents with two different field corn backgrounds, a strategy which is contrary to the usual pattern of employing at least one parent with a sweet corn background. The novel combination of field corn parents has yielded an array of features which render it preferable to the known sweet corn varieties with respect to both consumer and agronomic characteristics.

3. BRIEF DESCRIPTION OF THE INVENTION

The present invention provides a corn or supersweet corn hybrid wherein the hybrid is obtained by crossing a parent population having a dent background preferably as male with a parent population having a flint background preferably as a female.

The invention also provides a method of producing a sweet or supersweet corn hybrid which comprises crossing a parent population having a non-sweet corn background with a second parent population having a non-sweet corn background different from the first parent.

The invention also provides processed products made from the sweet corn hybrids of the invention for example, flour and corn snacks made therefrom, as well as whole dried kernels In a preferred embodiment the corn hybrids used are of the "supersweet" type.

4. BRIEF DESCRIPTION OF THE FIGURES

5. DETAILED DESCRIPTION OF THE INVENTION

Figure 1:
FIG. 1 shows a comparison of the husk tightness observed in a flint x dent hybrid having the genotype $SuSush_2sh_2$.

As noted above, the current wisdom in improved sweet corn breeding is to use at least one parent having a sweet corn background, with the necessity for accepting the attendant problems of low yield and germination rates. It has now been unexpectedly found that it is possible to employ two field corn parents of different backgrounds, and obtain progeny having sweetness equivalent to sweet corn or supersweet corn, and yet having agronomic characteristics superior to those of sweet corn.

5.1. CHARACTERISTICS OF HIGH YIELD HYBRIDS

In the hybrids of the present invention, the problems of low yield and poor germination observed with the presence of the su allele are obviated by the use of a flint parent as female and a dent parent as male to produce the hybrid. Thus, any hybrid (i.e., flint x dent) containing the su allele is improved in both yield and germination rate. However, the advantage of the present invention is particularly achieved in a combination in which the shrunken-2 ($sh_2$) allele is present. As noted above, the presence of the shrunken allele has the effect of increasing sucrose content thereby producing "supersweet" corn lines. However, the decrease in starch content in combination with the higher sugar content has an even greater detrimental effect on the germination rate of the seed by reducing kernel energy reserves needed for germination. (Boyer et. al., *Plant Breeding Reviews*, Vol. 2, p. 139-16., 198). This poor germination, and reduced yield observed in the supersweet lines has been in large part responsible for the lack of large-scale commercial acceptance of the supersweet lines containing the $sh_2$ allele. However, the combination of the flint x dent cross unexpectedly provides a hybrid which compensates for these disadvantages, allowing the production of a supersweet corn line which has yield and germination rates equivalent to the more hardy field corn types. Thus, the present invention provides a means by which corn lines having very desirable consumer and processing characteristics, i.e., a high sugar and sucrose content, may be produced in commercially useful quantities. The high yields and increased germination rates observed in the present hybrids thus make it possible to produce very sweet corn in quantities sufficient for commercial processing into corn based products such as corn flour which is in turn used in the preparation of corn chips, muffins, cereals and the like, as well as corn snacks directly from the dried corn kernels; such utility has not heretofore been feasible with the low yielding sweet and supersweet corn previously available. Even more surprisingly it has been found that it is possible to achieve a high yielding supersweet corn hybrid without the presence of the sugary (su) allele. It has now been observed that a flint x dent hybrid having the genotype $SuSush_2sh_2$ has all the desirable characteristics of the currently available supersweet corn hybrids, with none of the attendant disadvantages of low yield and poor germination.

To clarify the following discussion, some initial definitions are necessary. As used in the present specification and claims, the term "supersweet" refers to any corn variety, the endosperm of which routinely contains greater than 20% sugar within 21-30 days following pollination, regardless of whether it is a field corn or a sweet corn background. "Sweet corn," as already noted, refers to a corn germ plasm containing the sugary (su) allele. As used herein, the term "sweet corn" will refer to a germ plasm containing at least 8%, but usually no more than about 15% sugar at 21-30 days after pollination.

Those skilled in the art will recognize that sugar content begins to drop after its peak period for consumption, which varies somewhat from one type of corn to the next, but which is predictable within a given type of corn.

Cultivated corn (Zea mays) is commonly divided into several groups based on variations in the endosperm characteristics of the kernel. The most commonly recognized subgroups are dent, flint, flour, sweet, pop and pod. Of particular interest to the present invention are the flint and dent types, which are collectively often referred to as field corns, and are the corns most commonly used for food and feed purposes. As used herein and in the specification and claims, "flint" and "dent" are intended to encompass lines which are partially flint- or-dent derived, but which retain the flint or dent characteristics which confer the benefit to the present hybrids.

5.2. DENT CORN

Dent corn is the most commonly grown type of corn in the United States. This type of corn is characterized by a vitreous, horny endosperm at the sides and back of the kernel, with a central core extending to the crown of the kernel being soft and floury. The name derives from the distinct depression or dent which arises in the crown of the kernel resulting from rapid drying and shrinkage of the soft starch during grain maturation. The dents currently grown in the United States are typically Southern or Corn Belt dents. A number of valuable tropical dents, for example the Mexican Dents (including the Tuxpeno Page) and Tuson, are also available. A more thorough summary of known dent lines can be found in Brown and Goodman, "Races of Corn" in *Corn and Corn Improvement*, G. Sprague (ed.), Amer. Soc. Agron. 1977.

5.3. FLINT CORN

Flint corn is the most commonly grown corn in Europe and Asia, and is particularly popular in South and Latin America. The kernels are characterized by a high proportion of thick, hard vitreous endosperm surrounding a small granular center. The relative amounts of soft and vitreous starch may vary among corn strains. Externally, the flint kernels are smooth and rounded, with no denting. The flint lines available in the United States generally belong to one of the three following complexes: Northern Flints, Great Plain Flints, and Southeastern Flints. A more detailed discussion of the various flint varieties currently in existence can be found in Brown and Goodman, supra.

5.4. FLINT X DENT HYBRIDS

The present invention can be employed with any genotype which confers sweetness or supersweetness to a corn line. Those genotypes included are those containing su in the heterozygous or homozygous states, those containing $sh_2$ in the heterozygous or homozygous state, and heterozygotic and homozygotic combinations of the su and $sh_2$ allele. A particularly useful genotype in the present invention is the genotype Su-Sush$_2$sh$_2$. The success of the genotype is especially surprising because it does not contain the su allele at all, and yet produces a corn line which has sweetness equivalent to known "supersweet" corn lines, but, because of the flint x dent parentage, does not have the disadvantages attendant upon the use of either the su or $sh_2$ alleles.

Although individual hybrids may differ in their overall characterization, depending on the identity of the parents, all hybrids of the present invention will have certain characteristics in common. For example, all the present flint x dent hybrids homozygous for genes which block starch synthesis will have a sugar content of at least about 8%, and preferably, when the genotype is SuSush$_2$sh$_2$, will have a sugar content of at least about 20–30%. Further, the present hybrids all have an improved germination rate, relative to known sugary and supersweet varieties. The germination rate is consistently at least about 80%, and preferably averages at least about 90%. Finally, the overall yield is substantially improved, and more closely approaches normal field corn yield at the milk stage, than to either sugary or sweet corn varieties. Field yield of the present hybrids is always at least 8 and up to 18 or more metric tons per hectare, with the percentage of useable ears generally being at least about 80% and preferably about 85–90% (see Table 1).

5.4.1. SUPERSWEET SuSush$_2$sh$_2$

As already mentioned, it is not unknown TM to use the $sh_2$ allele to increase endosperm sugar content in combination with either the Su or su allele. However, it has now been discovered that the use of the genotype SuSush$_2$sh$_2$ in parents of different non-sweet corn background can produce an improved hybrid which is superior to both traditional field corn and sweet corn in the resulting combination of increased sweetness and hardiness in the field. The progeny produced by crossing a flint parent with a dent parent has proved to have particularly appealing characteristics. The flint x dent SuSush$_2$sh$_2$ hybrid exhibits a range of sugar concentration of about 20–36%, with an average sugar content of about 28%; within this range, sucrose constitutes about 18–26%, averaging about 24% on a dry weight basis at 25–30 days after pollination, essentially equivalent to or greater than that found in a typical supersweet corn variety. Of particular interest, however, is the unusually high germination rate, typically at least 80% and frequently as high as 95%, which is a substantial improvement over sugary shrunken (i.e., sush$_2$) hybrids that routinely have a germination as little as 10–70%. In a typical plant homozygous for the shrunken-2 allele, the volume of endosperm is drastically reduced, thus altering the endosperm:embryo ratio, decreasing the amount of available nutrition for the embryo, and reducing the chances for successful germination. The use of the flint parent as female, however, unexpectedly appears to counteract the effect of the shrunken gene, as far as endosperm volume is concerned, so that the ratio is returned to normal; thus germination is not adversely affected, and loss due to mechanical harvesting and planting of seeds is substantially avoided. Further advantage is obtained in that because cracking of the seeds does not occur, pathogens are unable to gain access to inner seed tissue.

Another interesting feature of this invention is that yield is substantially increased in this hybrid. Typically, yield will range from at least about 8–25 or more metric tons, averaging at least about 12–15, per hectare of ears (average of at least about 7–10 metric tons/acre at the fresh stage for consumption. Of this total yield, at least about 80%, and up to 90% or more, are useable ears. In both field yield and useable yield, then, the present hybrids are superior to known supersweets. (See Table 1). This represents a productivity which is about 30% higher than other supersweet corn hybrids. A reason for this high yield may be related to the high heterotic response of flint x dent crosses and to the hybrids, longer maturity (about 15 days longer) which allows for a longer period of synthesis and accumulation of dry matter. The flint x dent combination also recovers the kernel depth of the sweet corn types and provides a product having very crunchy or crispy kernels, which in turn provides greater protection against mechanical damage during transport as well as an appealing consumer characteristic. An additional benefit of the present combination is the presence in the hybrid of substantially more fiber than is found in sugary or ordinary field corn and somewhat higher than certain supersweet varieties (See Table 2). An average minimum of about 6% fiber is typical for the present hybrid.

TABLE 1

Comparison of yield of supersweet corn of the present invention, sugary corn (susuSh$_2$Sh$_2$; supersweet (susush$_2$sh$_2$); and field corn (SuSuSh$_2$Sh$_2$)

| Material | Field Yield (MT/Acre) | % Useable Ears |
|---|---|---|
| "Maizingly Sweet" | 7.2 | 90 |
| Sugary | 6.7 | 75 |
| Supersweet | 5.4 | 75 |
| Field Corn | 12.0 | 80 |

5.4.2. TROPICAL SUPERSWEET HYBRIDS

In one embodiment of the present "supersweet" lines, at least one of the two parents is derived from tropical field corn germplasm. The resulting hybrid has a substantial level of insect resistance conferred by the hybrid characteristic of husk tightness, a feature best understood by reference to FIG. 1. The tightness of the husk prevents invasion of the ear by insect as well as fungal pathogens which cannot easily find entry into the ear. This feature is a contribution of the flint parent and resistance make an attractive candidate as a parent in development of new supersweet corn lines.

With respect to the dent parents, virtually all tropical dents are members of the "Tuxpeno" race or derivatives thereof. In a preferred embodiment, the dent parent is a Tuxpeno into which the $sh_2$ gene, as well as the Cateto gene for orange color, has been introduced. Although the identity of the parent plants is not critical, it is preferred, in any of the present hybrid crosses, that the female parent be flint since this combination provides better support for seed set against disease.

TABLE 2

Comparisons of pertinent characteristics of the hybrid of the present invention (intervarietal hybrid) with sugary shrunken (USA X-Sweet), sugary, and field corn lines. Each type was analyzed at its peak stage for consumption.

Figure 2:
FIG. 2 shows the relative resistance of a hybrid to disease and insect resistance when compared with a normal supersweet corn under the same conditions.

| GENOTYPE | MOISTURE % | PROTEIN % dw | FAT % dw | FIBER % dw | DIG. CH. % dw | CAROTENE IU/100 g dw | TOTAL SUGARS % dw | SUCROSE % dw | FRUCTOSE % dw | GLUCOSE % dw |
|---|---|---|---|---|---|---|---|---|---|---|
| Intervarietal Hybrid | 72 | 14 | 6.4 | 6.4 | 71 | 1700 | 28.0 | 24.0 | 1.4 | 2.5 |
| USA X-Sweet | 76 | 15 | 5.4 | 5.0 | 72 | 1100 | 29.2 | 25.0 | 1.7 | 2.5 |
| Sugary | 74 | 13 | 2.0 | 3.1 | 78 | 200 | 8.0 | 3.8 | 1.5 | 2.7 |
| Field Corn | 63 | 11 | 2.4 | 2.4 | 82.2 | | 6.7 | 3.0 | 1.6 | 2.2 |
| Freeze-dry Flour from Intervarietal Hybrids | 6.6 | 14.2 | 9.6 | 3.2 | 70.3 | | 33.6 | 27.2 | 2.7 | 3.7 | can be found in many types of potential flint parents. Similarly, such hybrids have a gene-based resistance to various fungal and foliar disease such as Northern and Southern Leaf Blight, Common rust, Anthracnosis and *Helminthosporium carbonum*. Thus, not only is overall yield improved in the flint x dent hybrids, but also the average number of usable ears is improved due to the inherent disease resistance provided when at least one tropical parent is used. Generally speaking, an average of about 90% usable ears are obtained from the typical hybrid crop. The difference that this combined insect and fungal resistance makes in the ultimate quality of the crop and its yield can be seen by reference to FIG. 2 and the accompanying legend. The desirable characteristics of the tropical flints and dents can of course be easily bred into temperate flint or dent lines, and for this reason, when the term tropical germplasm is used in the present specification and claims, it is intended to encompass any line the breeding history of which includes a tropical parent or parents.

As just noted, the use of tropical germplasm provides certain distinct advantages relative to disease resistance, and this is one preferred embodiment of the present invention. Even in the case of using tropical flint and dent parents, however, the choices are not particularly limited. A large number of different races of both tropical flints and dents are currently available. Among the more common flints available are "Eto," "Antigua," "Puerto Rico," "Coastal Tropical flint," and "PDMS." A particularly preferred flint parent is one of the "Cateto" race, which is indigenous to South America. Certain highly desirable features, such as resistance to acid soils and insect resistance are characteristics of Cateto inbreds.

In one embodiment, the flint parent is a novel Cateto line into which the $sh_2$ gene has been introduced. A L. supersweet flint line having the genotype $SuSush_2sh_2$ has not previously been known, and the natural husk tightness, deep orange color (i.e., an average carotene content of greater than 1200 IU/100 g, and preferably about 1300–2000 or more IU/100 g) and foliar disease As examples of the present hybrids, two useful supersweet hybrid lines are described herein. One is an intervarietal hybrid line which has been obtained by crossing of synthetic populations of a Cateto supersweet orange flint and a Tuxpeno supersweet orange dent. The details concerning the synthesis of the individual populations and the resulting intervarietal hybrid is found in Example 1. A second is an inbred hybrid, also having parents with Cateto flint and Tuxpeno dent backgrounds. The details concerning its breeding are presented in Example 2. A preferred supersweet hybrid line is characterized by an attractive deep orange kernel color, a high germination frequency, resistance to seed damage during harvesting, mechanical processing, planting and shipping, and higher useable yields per acre, greater disease resistance (both fungal and insect) and higher fiber content than typical sweet corn "supersweets."

As noted above, the reduced vigor, germination rate and low yield observed with sweet corn, and especially supersweet corn, has prevented their large scale use in processed products. There is a great demand in the food industry for corn-based products, particularly flour, for use in preparation of cereals, muffins, breads, cakes, meal, crackers, corn chips, tortilla chips and the like. Corn snacks can also be prepared directly with the individual kernels, for example, a dried corn kernel snack. However, it is impossible to employ sweet and supersweet corn on a commercially feasible scale because of the relatively low volume which can be currently produced economically. Therefore, the present corn-based products typically employ the abundantly available field corn as the source of corn flavor. The field corns which are grown in the United States, however do not have the level of sweetness which would be desirable in a number of the aforementioned products.

The present invention has now provided a means by which sweet and supersweet corn can be produced in volumes equivalent to regular field corn, therefore, it is now possible to employ sweet or supersweet corn as the basis for a number of known types of corn products. The flour and corn products produced from the corn hybrids described herein are thus considered as an integral part of the present invention.

The sweet corn products of the present invention are prepared from either fresh or dried sweet or supersweet corn precursor materials described below, in accordance with methods known in the art.

The dried corn products of the present invention may be provided in the form of (a) dried cobs or ears with the dried kernels attached thereto, (b) dried whole kernels, in individual form, or in the form of compacted cakes of such kernels, (c) flour made from fresh or dried kernels, and (d) compounded or formulated products made with such flour, such as leavened and unleavened bread, cakes, breakfast cereal, muffins, pancakes, milk shakes, pudding, fillings for pastry and pie, ice cream, beverages, salad dressing, sausage filling, crackers, or chips.

The dried kernels may be removed from the cob and eaten as such, or they then be compressed together, with or without a food grade adhesive type materials, to form cakes of the kernels which could be one or more layers (of kernels) thick. In a preferred embodiment, an agglomerated bar or cake is prepared using a paste prepared from fresh or partially dried kernels mixed with water, preferably in about a 1:1 ratio, and tumbling or mixing the paste with dried kernels. The kernels can be eaten when at ambient temperatures or they may be warmed up, as by being heated in a microwave oven, or other heating device. Thin cakes of the kernels may be heated or toasted in a toaster.

The dried kernels may also be used in loose or agglomerated mixtures with one or more other components of snack type products such as dried fruit, such as raisins or diced dried peaches, figs, pears and the like, whole, or piece-firm, nuts such as peanuts, cashews, pecans, walnuts, and seeds such as sunflower seeds.

Flour may be made from the kernels after the kernels are dried in the field, using conventional corn flour-making processes and equipment. However, in a preferred embodiment, a flour-type product is prepared from the fresh kernels directly without drying. In this embodiment, the fresh kernels are harvested at the milk stage, and processed in a drier, substantially identical to the method used to produce instant mashed potato flakes. Prior to processing in a drier the fresh kernels are ground into a paste. This paste may be sieved to remove the pericarp portion, and leaving a thinner, more soluble paste. Both the pericarp fraction and the soluble fraction may also be used as the paste base for the drying procedure. The corn flour products so produced, because they are prepared from fresh rather than dried kernels, retain a higher proportion of the fresh corn's natural sweetness. This usually sweet corn flour product can be employed alone in the manufacture of products requiring a cereal flour, or may be used in mixture with dried corn or wheat flour. Each different fraction is useful in a different type of product: for example, the first paste, which contains both soluble and insoluble fractions, will be useful in products like creamed corn cereals; the pericarp fraction which is about 60–80% fiber, is particularly preferred as the corn flour base in crackers and dry cereals. Finally, the most soluble fraction is preferably used in products such as ice cream and corn flavored beverages. It will be readily apparent to those skilled in the art what other variations on use are available with the present corn flour. Such a naturally sweet corn flour, made either from fresh or dried kernels, has not previously been available primarily because of the inability to grow significant quantities of supersweet corn for commercial flour production. As used throughout the specification and claims, the term "flour" or "corn flour" is intended to encompass all the aforementioned types of flour and obvious variations thereof.

In one embodiment the flour or dried kernels of the present invention is derived from the bright yelloworange kernels of the hybrid described above. The increased carotene content of the kernels of this hybrid provide an attractive natural yellow corn color to the end products.

The sweet corn flour of the present invention can be used as a base for various types of formulated products. In all of these products the corn flavor provided by the flour could be the primary, if not the sole flavorant used therein, and would be a completely natural source of such flavorant. In all of these products the sweetness provided by the corn flour could be the primary if not the sole, source of sweetness for the end products, and would be a completely natural source of such sweetness.

Various of these flour based products would be made as follows:

A mashed sweet corn product, similar to mashed potatoes made from dried potato flakes, may be made by adding hot or cold water to a water soluble, preferably, flour fraction until a desired consistency is obtained.

Pudding type dessert products may be made by mixing a water soluble, preferably, flour fraction with hot or cold milk, food grade thickening agents such as wheat flour, and, optionally, other sweeteners, until the desired consistency of the product is obtained.

The water soluble, preferably, fraction of the corn flour may be used as a filling for pies or other pastry products. The filling would be made in the form of the mashed or pudding products described about. Such fillings could be used as freshly made, or after being frozen.

The flour may be added in flavoring amounts to ice cream formulations. A water soluble fraction is preferably used. When added to an already made and otherwise flavored ice cream product, the corn flour is preferably added to vanilla flavored, or other mildly flavored, ice cream, so as not to mask the desired corn flavor of the flour, in a ratio of up to 1:1. The dried whole kernels may also be added to ice cream, as a supplement or replacement for other particulated fillings used in ice cream such as chocolate chips, praline candy, sprinkles, fruit, and the like.

Milk shakes may be made by adding flavoring amounts of a water soluble, preferably, fraction of the corn flour to the milk and thickening agents normally used in such products.

A corn beverage may be made from a water soluble fraction of the corn by admixing about the flour in hot or cold water.

Salad dressings may be made with the flour in any form as a flavorant or filler, in combination with other components normally used in such fillings.

Crackers, or other dried baked products such as pretzels or breadsticks may be made, preferably with a water insoluble fraction of corn flour. An insoluble corn flour fraction can be used to provide the final products with a naturally high fiber content. The products may be formulated with other components normally used therein such as wheat flours, other sweeteners, and salt, for salty versions thereof.

Unleavened cake type products may be prepared with, preferably, an unfractionated flour. The unleavened cake type products would include thin cake type products such as tortilla or corn chip products. Corn bread, corn muffins or corn pone type products may also be made. Corn flakes may be made from the flour by toasting flakes.

The following non-limiting examples illustrates an example of a hybrid of the present invention, and products derived therefrom.

6. EXAMPLE 1: INTERVARIETAL HYBRID

The following discussion demonstrates the method by which the synthetic parental populations were obtained.

6.1. SUPERSWEET ORANGE FLINT SYNTHETIC

6.1.1. POPULATION SYNTHESIS

Three varieties of the tropical race Cateto were used for the synthesis of this population. It is an authochthonous race distributed along the southern coast of Brazil and Argentina. It has very translucid deep orange color endosperm with round kernels like popcorn, though the seeds are larger.

This race is known by its high rusticity. It was cultivated by former settlers and under low tech farming conditions. Some of the advantageous features which have established its popularity are that it yields well in poor soil (low pH), has resistance to the main foliar diseases (*Helinthosporium turcicum, Puccinia sorghii* and *Phaeosphaeria sp*), and it has husk tightness which protects the ear against ear worm, weevil and moth.

6.1.2. INTRODUCTION OF THE $sh_2$ GENE

Cateto was crossed with $W_{23}$ $sh_2$ stock and backcrossed twice. About 400 ears of the best plants were selfed. The segregating ears with deep yellow shrunken kernels were chosen, and the mutant seed was planted in an isolated lot. From 186 progeny planted in the field, 30% were eliminated before flowering due to such undesirable agronomic traits as lodging, high ear insertion and foliar disease susceptibility.

At harvesting, from the best five plants of each progeny were taken 20 kernels to reconstitute the population.

6.1.3. RECURRENT SELECTION

For four generations, a phenotypic recurrent selection (stratified mass selection) was done in an isolated block. Before flowering, the plants with undesirable agronomic traits were eliminated, and only the selected ones (about 10% of selection intensity) were allowed to pollinate openly. At harvest, only healthy ears with deep orange colored kernels and very tight husk cover were selected to reconstitute the balanced composite. This cycle was completed for four generations to achieve the supersweet orange flint synthetic.

This population has been deposited with the american Type Culture Collection under Accession Number ATCC 40736.

6.2. SUPERSWEET ORANGE DENT SYNTHETIC

6.2.1. POPULATION SYNTHESIS

Six tropical synthetic populations were used for the synthesis of the dent population. All of them are true Tuxpeno germplasm, except for one which has 50% of Cateto germplasm. This population has been deposited with the American Type Culture Collection under Accession Number ATCC 40735. This population was assembled through the cross of a three-way cross involving the six above-mentioned synthetics. The synthetic population so formed was open pollinated in an isolated block for two generations to reduce linkage disequilibrium. The final population has typical cylindrical ears of the Tuxpeno race with yellow endosperm.

6.2.2. INTRODUCTION OF THE $sh_2$ GENE

The donor gene stock was a Cateto $sh_2$ synthetic with deep orange color. The $sh_2$ gene introduction was done by backcrossing followed by selfing for two generations to allow an increase in gene frequency for high carotene accumulation in the dent kernels.

As the cylindrical ears were recovered, the backcrossing program was terminated.

6 2 3. RECURRENT SELECTION

Four cycles of progeny selection were performed on this supersweet orange dent synthetic for agronomic traits. The selection was done in an isolated block. About 400 progeny were derived from desirable $sh_2$ homozygous ears, and about 40 were selected before flowering, on the basis of standability, foliar disease and insect damage resistance, and ear insertion. At harvest, 10 ears out of 50 were chosen within the selected 40 progeny, and 75 kernels were taken from each to derive the 400 progeny to be planted in an isolated block. From each of the 400 ears were also taken 20 kernels, and a composite was made which was used as the male in the isolated detasseling block. The field was set up in a proportion of 4 female progeny to 1 male. At harvest, only selected ears with deep orange color were chosen to continue selection. Three more cycles of recurrent selection, as mentioned, were done in the following years.

Crossing of the two supersweet synthetic parent populations produce a hybrid according to the present invention. The intervarietal hybrid achieved by combination of the flint and dent parents is particularly advantageous because of the high heterotic response and the observed complementation of desirable traits found in the two parental populations. Table 2 shows a comparison between the flint parent, and dent parent, and the intervarietal hybrid for a number of traits. The hybrid has been given the variety designation "Maizingly-Sweet" and seed has been deposited with the American Type Culture Collection under Accession Number ATCC 40434.

TABLE 3

Comparisons of certain traits among the flint parent, dent parent, and the intervarietal hybrid produced by the cross of the flint and dent parent.

| Characteristics | SSOFS (flint) | SSODS (dent) | ISSH |
|---|---|---|---|
| Yield (MT tons/ha) | 10 | 11 | 12 |
| Ear Length (cm) | 16–18 | 18–20 | Intermediate |
| External Ear Diameter (cm) | 3.6–4.0 | 4.0–4.2 | Intermediate |
| Internal Ear | 2.6–2.8 | 1.8–2.0 | Intermediate |

TABLE 3-continued

Comparisons of certain traits among the flint parent, dent parent, and the intervarietal hybrid produced by the cross of the flint and dent parent.

| Characteristics | SSOFS (flint) | SSODS (dent) | ISSH |
|---|---|---|---|
| Diameter (cm) | | | |
| Ear Shape | Conical | Cylindrical | Intermediate |
| Kernel Rows | 10–12 | 12–14 | Intermediate |
| Kernel Shape | Round | Round | Intermediate |
| Kernel Length (mm) | 5–7 | 10–12 | Intermediate |
| Kernel Color | Orange | Orange | Orange |
| Brix | 13.0 | 11.8 | 13.0 |
| Al+++ Tolerance (4 ppm) | Tolerant | Susceptible | Tolerant |
| Seed Injury (harvesting and planting) | None | High | None |
| Germination (%) | 90% | 80% | 90% |
| Yield Index* (y) | 5450 | 3886 | 5774 |

*$y = (E^2 - I^2).L.X$
where:
x is usable ears
E is external ear diameter
I is internal ear diameter
L is ear length

7. EXAMPLE 2: TOP CROSS HYBRID

In addition to the intervarietal hybrid described above, a top cross hybrid has also been prepared. This hybrid has all the advantages of the intervarietal hybrid, but also has the added advantage of uniformity in the population particularly with respect to the deep orange color, and a resistance to the plant disease caused by Fusarium sp. The parents of the hybrid are the improved supersweet orange flint synthetic derived from the supersweet orange flint synthetic described in connection with the intervarietal hybrid, and a semi-dent inbred. The method of obtaining the hybrid is outlined below.

7.1. IMPROVED SUPERSWEET ORANGE FLINT SYNTHETIC

The supersweet orange flint synthetic was prepared as described in the development of the flint parent for the intervarietal hybrid through the point of the first recurrent selection. A second phase of recurrent selection was then performed on the population so obtained: the population was submitted to two cycles of selection to enhance carotene content in the kernels providing a deeper orange color in the $sh_2$ endosperm.

About 1000 plants were then selected for lower ear insertion, resistance to foliar disease, such as Common Rust, Northern Leaf Blight, Southern Leaf Blight and Helminthosporium carbonum, before flowers were bagged and selfed. At harvest, 40 ears with no insect injury, and good husk protection and with uniform deep orange color were chosen for further selection. In an isolated block, these 40 progeny were planted, and from this group the 20 less uniform rows having less desirable characteristics such as lodging, susceptibility to foliar disease and plant height taller than 3 meters were eliminated before flowering. The remaining 20 progeny were open pollinated. At harvest, 20 kernels having the deepest orange color were selected from the four best plants of the selected progeny, to form a balanced composite. A second cycle, exactly as described above, was immediately performed. As a result of the selection procedure, the final population had greater uniformity in plant height (about 3 m), ear height (about 1.7 m) and enhanced orange color in the endosperm (carotene content of at least about 1200 IU/100 mg).

The resulting population also had such desirable traits as compact husk cover, ear worm resistance, ear length of about 20 cm, no lodging, no anthocyanin, a germination ratio higher than 90% and resistance to common rust, and Northern and Southern Leaf Blight.

7.2. INBRED LINE MT-107 $sh_2$

The second parent is a field corn inbred derived from a typical synthetic containing 25% of germplasm of the Cateto race, and 75% of yellow dent Tuxpeno race. It was selected originally with a semi-dent endosperm and has extremely high resistance to Fusarium sp., guaranteeing a high stalk quality and high ear rot resistance. The plant averages around 2.8 meters in height, and the ear, having 14 kernel rows, is inserted at about 1.4 meters from the ground. The orange colored kernel is about 6 mm long; the inbred has no anthocyanin, tassels with 8 to 12 branches, and a silk delay of three days.

In addition to the advantages noted above, i.e., the deeper orange colored kernels, and resistance to kernel rot pathogens, the hybrid obtained by the crossing of the supersweet orange flint synthetic and the inbred MT-107 is characterized as shown in Table 3. This hybrid has been given the designation "Maizingly-Sweet 2", and seed has been deposited with the American Type Culture Collection under Accession Number ATCC 40435.

TABLE 4

Comparable traits of the parentals, improved Supersweet orange flint synthetic (improved SSOFS) and inbred MT-107 $sh_2$, and the resultant uniform single hybrid.

| Characteristics | Improved SSOFS | MT-170 $sh_2$ | Top Cross Hybrid |
|---|---|---|---|
| Yield (MT tons/ha) of fresh corn on the husk | 12 | 6 | 14 |
| Ear Length (cm) | 18 | 15 | 17 |
| External Ear Diameter (cm) | 3.6–4.0 | 3.2–3.5 | 4.0–4.2 |
| Ear Shape | Conical | Cylindrical | Intermediate |
| Kernel Rows (No.) | 10–12 | 14 | 14 |
| Kernel Shape | Round | Round | Long |
| Kernel Length (mm) | 6–8 | 6 | 10–11 |
| Plant Height (cm) | 3.0 | 2.8 | 3.0 |
| Ear Height | 1.7 | 1.4 | 1.5 |
| Brix | 13.0 | 13.0 | 13.0 |
| Al Tolerance at 4 ppm | Tolerant | Susceptible | Tolerant |
| Seed Injury | None | None | None |
| Germination (%) | 90% | 90% | 90% |
| Yield Index | 5,400 | 1,860 | 6,061 |

8. EXAMPLE 3: DRIED CORN PRODUCT

The fresh sweet corn which was employed in the following Examples was a supersweet corn hybrid as described in 6.1 above. This fresh corn product was harvested about 25 days after pollination and had, at such time, the following composition:

| Sweet Corn Component | Weight % |
|---|---|
| Moisture | 72 |
| Total Sugars | 28 |
| Sucrose | 24 |
| Fat | 6.4 |
| Fiber | 6.4 |
| Digestible Carbohydrates | 71 |
| Carotene | 1700 IU/100 grams |

When the kernels are to be obtained in dried form, they are first removed from the cobs using conventional procedures for removing the kernels from the cobs, and then they are also dried using the drying procedure described below. When it is desired to make flour from the corn, the flour may be made directly from the fresh corn using a desirable drying procedure, or the flour may be made by grinding the dried kernels. The method of drying the kernels may be any of those known in the art, but the method described below provides a relatively economical and simple means for drying in the appropriate manner.

In order to expedite the drying of the kernels, on- or off-the-cob, the kernels are pre-treated with an alkaline or acid medium designed to perforate the hulls of the kernels during the pretreatment process so as to, subsequently, provide for a more rapid removal or mass transfer of moisture from the kernels during the subsequent drying operations. This soaking or pretreatment procedure results in a significant shortening of the drying time that might otherwise be needed, when using prior art vegetable drying techniques, to achieve the same end result, in terms of final moisture content in the dried kernels. This shortened drying time avoids subjecting the kernels to excess heat treatment and thus preserves the taste, texture and appearance of the dried kernels.

In the pre-treating or soaking step in the process, the kernels, on- or off-the-cob, are soaked in a hot, i.e., about 170° to 220° F., aqueous bath of an alkaline or acid medium for about 1 to 3 minutes. A typical alkaline medium is about 0.5-1% solution of NaOH. A typical acid solution would include citric acid.

After the kernels are thus treated in the soaking bath, they are then rinsed with water, and any residual alkaline or acid values are neutralized with respectively, aqueous acid or alkaline, using the acid or alkaline agents noted above, but in a more dilute form.

The period of time needed for the soaking varies with the strength of the soaking medium and the speed with which the drying process is to be conducted. The more severe is the soaking process, in terms of time, and strength of the soaking bath, employed, the shorter will be the drying time needed, under the same drying conditions of time and temperature, to achieve a desired final moisture content in the dried product.

The presoaked kernels are then partially dried, to a water content of about 40 to 60 weight % in a direct or indirect fluidized bed drier operated batchwise or continuously. The partially dried kernels are then further dried, to a final moisture content of about 10 to 20 weight. An alternate form which may be used for the corn is an agglomerated cake or bar. These agglomerated cakes are formed by adhering the individual fresh, or partially or fully dried kernels together under slight pressure while the kernels are held together by a food grade adhesive type material. This food grade adhesive type material may be formed from a heated aqueous mash of the ground up corn. Such a mash can be prepared by grinding up or blending about 50 to 90 weight % of the fresh corn kernels with about 10 to 50 weight % of water to a pasty consistency and heating or cooking the paste to provide a corn flour based paste. The cooked aqueous mash is then admixed with the semi-dried corn kernels and this admix is then poured into molds to form the desired cakes for freeze drying. The thus molded cakes solidify at room temperature (~20°-25° C) with or without any added pressure. The cakes are then freeze dried. After freeze drying, the cakes may be packaged and merchandized and used as such, or the cakes can be broken up, at any subsequent time to provide individual kernels.

A batch of the fresh supersweet corn kernels were prepared as in Example 1 (with a moisture content of about 78%). This batch of kernels was then presoaked and dried in accordance with the soaking and drying process of the present invention. The kernels were first soaked in a hot (200° F.), 1% aqueous sodium hydroxide solution for one minute and then rinsed with water, and then soaked in 5.0% aqueous citric acid for 0.5 minutes at 20°-25° C. and rinsed again with water. The kernels were then partially dried to a moisture content of 25%-40% in a fluidized bed. The partially dried kernels were then further dried under the freeze drying conditions to a final moisture content of 15%. The resulting kernels were of a uniform acceptable color, texture and appearance. They had suffered no loss in color, were not shrivelled and were chewy, with a sweet corn flavored taste when chewed.

What is claimed is:

1. A corn hybrid, which is produced by crossing a field corn dent parent as the male with a field corn flint parent as the female, the kernels of which female field corn flint parent are characterized by a round shape and a thick starchy endosperm, said hydrob having kernels with a sugar content of at least about 20-30% at 25-30 days after pollination; (b) the genotype $SuSush_2sh_2$; (c) kernels with a germination rate of at least about 80%; and (d) an average fresh ear weight of at least about 6 metric tons per acre.

2. The hybrid of claim 2 wherein at least one parent is derived from tropical field corn germplasm.

3. The hybrid of claim 2 which is further characterized as having:
   (e) foliar resistance to Northern and Southern Leaf Blights, Common rust, Anthracnosis, and *Helminthosporium carbonum;* and
   (f) insect and fungal resistance due to husk length and tightness.

4. The hybrid of claim 3, wherein the flint parent is derived from the Cateto race and the dent parent is derived from the Tuxpedo race.

5. The hybrid of claim 4 which is further characterized as having:
   (g) kernels with a carotene content of at least about 1200 IU/100 grams.

6. The hybrid of claim 5 which is further characterized as having:
   (h) kernels with a length of about 10-11 mm at 25-30 days after pollination; and
   (i) ears about 8 inches in length with about 12-24 rows of kernels.

7. The hybrid of claim 5 which is further characterized as having
   (j) resistance to Fusarium sp.

8. The hybrid of claim 1, 2, 3, 4, 5, 6, or 7 wherein the germination rate of its kernels is at least about 85-90%.

9. Seed which produces the hybrid of claim 1.

10. Seed which produces the hybrid of claim 3.

11. Seed which produces the hybrid of claim 5.

12. Seed which produces the hybrid of claim 6.

13. Seed which produces the hybrid of claim 7.

14. Seed identified by ATCC Accession No. 40434.

15. A method of producing a corn hybrid which comprises crossing a field corn dent parent as the male with a field corn flint parent as the female, to obtain a hybrid having (a) kernels with a sugar content of at least about 2–30% days after pollination; (b) the genotype SuSush$_2$sh$_2$; (c) kernels with a germination rate of at least 80%; and (d) an average fresh ear weight of at least about 6 metric tons per acre.

16. The method of claim 5 wherein the flint parent is derived from a Cateto race, and the dent parent is derived from a Tuxpeno race.

17. A corn hybrid, which is produced by crossing a field corn dent parent as the male, with a field corn flint parent as the female, which field corn flint parent is derived from tropical field corn flint germplasm, said hybrid having (a) kernels with a sugar content of at least about 20–30% at 25–30 days after pollination; (b) the genotype SuSush$_2$sh$_2$; (c) kernels with a germination rate of at least about 80%; and (d) an average fresh ear weight of at least about 6 metric tons per acre.

18. A corn hybrid, which is produced by crossing a field corn dent parent as the male, with a field corn flint parent as the female, which field corn flint parent is characterized by (1) foliar disease resistance to Northern and Sourther Leaf Blight, Common rust, Anthracnosis, and *Helminthosporium carbonus*; and (2) insect and fungal resistance due to husk length and tightness; said hybrid having (a) kernels with a sugar content of at least about 20%–30% at 25–30 days after pollination; (b) the genotype SuSush$_2$sh$_2$; (c) kernels with a germination rate of at least about 80%; and (d) an average fresh ear weight of at least about 6 metric tons per acre.

19. The method of claim 15 in which the sh$_2$ genotype has been introduced into the male dent parent in a homozygous condition.

20. The method of claim 15, in which the sh$_2$ genotype has been introduced into the female flint parent in a homozygous condition.

21. The method of claim 15 in which the sh$_2$ genotype has been introduced into the male dent parent in a homozygous condition and introduced into the female flint parent in a homozygous condition.

* * * * *